United States Patent
Goutsis et al.

(10) Patent No.: US 10,357,436 B2
(45) Date of Patent: *Jul. 23, 2019

(54) SOLID-STABILIZED OXIDIZING AGENT PREPARATION, PRODUCT AND KIT FOR OXIDATIVELY CHANGING THE COLOR OF HAIR

(71) Applicant: Henkel AG & Co. KGaA, Duesseldorf (DE)

(72) Inventors: Konstantin Goutsis, Juechen (DE); Gabriele Weser, Neuss (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/584,935

(22) Filed: May 2, 2017

(65) Prior Publication Data

US 2017/0319442 A1   Nov. 9, 2017

(30) Foreign Application Priority Data

May 3, 2016 (DE) .................. 10 2016 207 570

(51) Int. Cl.

| | | |
|---|---|---|
| *A61Q 5/08* | (2006.01) | |
| *A61K 8/06* | (2006.01) | |
| *A61K 8/22* | (2006.01) | |
| *A61K 8/25* | (2006.01) | |
| *A61K 8/92* | (2006.01) | |
| *A61Q 5/06* | (2006.01) | |
| *A61Q 5/10* | (2006.01) | |
| *A61K 8/73* | (2006.01) | |
| *A61K 8/02* | (2006.01) | |

(52) U.S. Cl.
CPC ............ *A61K 8/062* (2013.01); *A61K 8/0241* (2013.01); *A61K 8/22* (2013.01); *A61K 8/25* (2013.01); *A61K 8/732* (2013.01); *A61K 8/922* (2013.01); *A61Q 5/065* (2013.01); *A61Q 5/10* (2013.01); *A61K 2800/413* (2013.01); *A61K 2800/4322* (2013.01); *A61K 2800/4324* (2013.01); *A61K 2800/88* (2013.01); *A61K 2800/882* (2013.01)

(58) Field of Classification Search
CPC . A61Q 5/10; A61Q 5/065; A61K 8/22; A61K 8/062; A61K 8/25; A61K 8/922; A61K 2800/4324; A61K 2800/88
See application file for complete search history.

(56) References Cited

U.S. PATENT DOCUMENTS

| | | |
|---|---|---|
| 3,920,883 A | 11/1975 | Yamada et al. |
| 4,767,741 A | 8/1988 | Komor et al. |
| 5,643,555 A | 7/1997 | Collin et al. |
| 5,651,793 A | 7/1997 | Hoeffkes et al. |
| 2002/0054890 A1 | 5/2002 | Gers-Barlag et al. |
| 2009/0252815 A1 | 10/2009 | Walzer et al. |
| 2015/0297481 A1* | 10/2015 | Wahler ..................... A61K 8/29 424/401 |

FOREIGN PATENT DOCUMENTS

| | | |
|---|---|---|
| EP | 0870495 A2 | 10/1998 |
| FR | 3015233 A1 | 6/2015 |
| FR | 3015234 A1 | 6/2015 |

OTHER PUBLICATIONS

UKIPO Combined Search and Examination Report GB1706931.1 Date of Search: Jan. 29, 2018; dated Jan. 30, 2018 6 pages.

* cited by examiner

*Primary Examiner* — Eisa B Elhilo
(74) *Attorney, Agent, or Firm* — James J. Cummings

(57) ABSTRACT

An oxidizing agent preparation (A) for oxidatively changing the color of keratin fibers, in particular human hair, is present in the form of an oil-in-water emulsion (O/W emulsion), and includes
(a1) an oil phase including one or more fat constituents (F),
(a2) a water phase,
(a3) hydrogen peroxide, and
(a4) at least one type of fine-grain particles (P) having a mean particle size of less than 200 μm (micrometers).
A product that includes the aforementioned oxidizing agent preparation (A) is packaged in the form of a storage container. A multi-component packaging unit includes the oxidizing agent preparation (A) also includes a separately packaged dye (B).

15 Claims, No Drawings

SOLID-STABILIZED OXIDIZING AGENT PREPARATION, PRODUCT AND KIT FOR OXIDATIVELY CHANGING THE COLOR OF HAIR

FIELD OF THE INVENTION

The present invention relates to an oxidizing agent preparation (A) for oxidatively changing the color of keratin fibers, which preparation is present in the form of an oil-in-water emulsion (O/W emulsion) and includes an oil phase, a water phase, hydrogen peroxide, and at least one type of fine-grain particles (P).

The present invention also relates to a product for oxidatively changing the color of keratin fibers, which product includes the aforementioned oxidizing agent preparation (A) packaged in a storage container. The present invention also relates to a multi-component packaging unit, in which the oxidizing agent preparation (A) is packaged separately from a dye (B).

BACKGROUND OF THE INVENTION

The use of emulsions is widespread in the field of cosmetics. An emulsion is understood to mean a finely distributed mixture of two normally immiscible liquids without visible segregation.

In an emulsion there is a finely distributed mixture of two liquids present, such as oil and water. Here, one of the liquids (phase) forms small droplets which are present distributed in the other liquid (phase). The phase which forms the droplets is referred to as the inner phase or also the disperse phase. The phase in which the droplets are floating is called the outer phase or also the continuous phase.

Emulsions belong to the disperse systems and differ from mixtures of miscible liquids. Emulsions are generally cloudy, milky liquids. In the case of emulsions that comprise a water phase and an oil phase, a distinction is made between oil-in-water emulsions (O/W emulsions) and water-in-oil emulsions (W/O emulsions).

Emulsions are thermodynamically unstable. The disperse (inner) phase tends to want to amalgamate by coalescence to form larger areas—here, the interfacial energy between the two phases is reduced. Emulsions used in the field of cosmetics, however, should be maintained usually over a specific period of time (between a few hours and a few years) and under specific conditions (for example within specific temperature and pH value ranges).

In order to stabilize the emulsion, an emulsifier, i.e. a surfactant or a surface-active compound, is thus generally used, which facilitates the formation of the droplets and counteracts a segregation (phase separation). Emulsifiers lower the interfacial tension between the phases by forming interfacial films at the phase boundary between oil and water, whereby an irreversible flowing together of the droplets (coalescence) is counteracted. Cloudy emulsions having a droplet size in the micrometer range are generally produced.

An emulsion can also be stabilized by the addition of specific solids. Solid-stabilized emulsions are often called Pickering emulsions, after their discoverer. S. U. Pickering demonstrated in 1907 that small particles which are better wetted by water than by oil can stabilize O/W emulsions. What is important for sufficient stabilization is that a mechanically stable solids film can form around the dispersed phase.

A cosmetic Pickering emulsion can be, for example, an emulsion which is stabilized by colloidal silica particles. These silica particles arrange themselves at the interface between the two phases (hydrophilic and lipophilic phase) and prevent the droplets of the disperse inner phase form coalescing (amalgamation of the droplets).

Pickering emulsions or solid-stabilized emulsions include particulate solids for stabilizing the emulsion—said solids can be used either instead of surfactants or also in addition to surfactants. A key advantage of solid-stabilized emulsions lies in the fact that the surfactant concentration in the emulsion can be heavily reduced. After reduction of the surfactant concentration, solid-stabilized emulsions or Pickering emulsions are also generally characterized by a very good long-term stability.

A further advantage of Pickering emulsions lies in their greater stability with respect to changes of the chemical medium, for example a change to the pH values or the salt concentrations.

The principle of the stabilization of cosmetic emulsions by the use of particulate solids is already known from the prior art. By way of example, EP 0987002 describes Pickering emulsions which are characterized by an oil phase, a water phase, and at least one type of microfine particle having a mean particle size of less than 200 nm. The emulsions of EP 0987002 should be suitable for use as cleansing emulsion, as face or body care preparation, as sunscreen product, or as deodorant, and in particular should have an improved skin compatibility.

Fine-grain W/O emulsions comprising oil droplets in the micrometer range, which are free from surfactants and are stabilized only by solids, are described in EP 0686391. Here, spherical polyalkylsilsesquioxane particles are used having a diameter of from 100 nm to 20 μm. In EP 870495 fine-grain O/W emulsions comprising oil droplets in the micrometer range are described, wherein here surfactants as well are used as emulsifiers in addition to fine-grain solids having a diameter of up to 200 nm.

In U.S. Pat. No. 3,920,883 and U.S. Pat. No. 4,767,741 surfactant-free O/W macroemulsions in the form of droplets having a particle diameter of the oil droplets in the range of 0.1 millimeters to several centimeters are disclosed, in which case fine-grain solids particles are likewise used as emulsifier.

In all of the aforementioned documents, emulsions are described that are produced as a mono-component product, i.e. the emulsion in question—whether a skin cream, sunscreen product, cleanser, or deodorant—is applied directly after removal from the container in which it is provided.

The use of solid-stabilized emulsions has not previously been known in cosmetic products of which the use requires the prior mixing of two or more separately packaged preparations.

Hair dyes, in particular oxidative hair dyes, are a known example of cosmetic products in which the user, before said products can be used, must first produce a ready-to-use mixture by mixing various preparations.

Oxidative color-changing agents usually comprise a first component, which includes the oxidizing agent. This first component is mixed with a second, separately packaged component. This second component for example includes an alkalizing agent and/or oxidation dye precursors, or what are known as developer components and coupler components. The developer components form the actual dyes under the influence of oxidizing agents or of atmospheric oxygen, either amongst themselves or with coupling to one or more coupler components. In order to prevent a premature, undesirable reaction with one another, the oxidizing agent (hydrogen peroxide) and the oxidation dye precursors (or the alkalizing agent) are expediently only brought into contact with one another immediately before use.

In order to produce a ready-to-use oxidative dye, the user must therefore mix the first preparation, which includes the oxidizing agent, with the coloring substances (i.e. the oxidation dye precursors and/or the direct dyes).

Both the oxidizing agent preparation (A) and the dye (B) (which includes the oxidation dye precursors and/or the direct dyes) are generally emulsions. Here, the viscosity of each emulsion must be selected such that both emulsions on the one hand are thin enough to ensure complete and homogenous mixing, but on the other hand are also sufficiently thick to avoid a dripping of the finished ready-to-use mixture.

Both the oxidizing agent preparation (A) and the dye (B) are thus set optimally to a precisely defined viscosity range.

Particularly in the field of hairdressing, the oxidizing agent preparation (A) is often supplied to the hairdresser in a large bulk bundle. In order to ensure a comfortable and quick removal, the oxidizing agent preparation (A) is often set to a very low viscosity. Emulsions of low viscosity in particular often have serious weaknesses in respect of their storage stability.

It is therefore desirable to provide an oxidizing agent preparation for oxidatively changing the color of keratin fibers, in particular human hair, which preparation is present in the form of an emulsion, can be set to a low viscosity range, and yet still has a very high storage stability. These oxidizing agent preparations should be able to be mixed particularly easily and quickly with a second preparation (for example a coloring cream), such that a homogenous ready-to-use mixture in the optimally set viscosity range is produced after the mixing. In addition, the viscosities of the oxidizing agent preparation and of the finished ready-to-use mixture should lie in the desired specification range, even after a longer storage time, i.e. the viscosities of oxidizing agent preparation and ready-to-use mixture should not change or shift unpredictably even after storage of the oxidizing agent preparation over a number of weeks. Furthermore, other desirable features and characteristics of the present invention will become apparent from the subsequent detailed description of the invention and the appended claims, taken in conjunction with this background of the invention.

BRIEF SUMMARY OF THE INVENTION

A first subject of the present invention is an oxidizing agent preparation (A) for oxidatively changing the color of keratin fibers, in particular human hair, which preparation is present in the form of an oil-in-water emulsion (O/W emulsion). The preparation (A) includes
(a1) an oil phase including one or more fat constituents (F),
(a2) a water phase,
(a3) hydrogen peroxide, and
(a4) at least one type of fine-grain particles (P) having a mean particle size of less than 200 μm (micrometers).

It has been found that the oxidizing agent preparations (A) of this type according to the invention are particularly stable under storage. In this way, the preparations could also be set to low viscosity ranges without the emulsion separating after a certain storage time and/or at low temperatures. By means of the use of the fine-grain particles (P), the viscosity could be set to a precisely defined range and could be reliably held in this range, even after a long period of storage. Further-more, it has proven to be particularly advantageous in this regard that the use of organic polymers having a thickening effect could be omitted in this way.

The oxidizing agent preparations (A) according to the invention are very particularly well suited for packaging in large bundles. Large bundles in particular—since they can be used for many applications—are often stored for longer than smaller bundles. So as to be able to ensure a simple and rapid removal of the required portions from the bundle, the setting of a low viscosity range is additionally particularly important in the case of this packaged form.

A second subject of the present invention is a cosmetic product for oxidatively changing the color of keratin fibers, in particular human hair. The product includes:
  an oxidizing agent preparation (A), which is packaged in a container (I), wherein
  the oxidizing agent preparation (A) is an oxidizing agent preparation of the first subject of the invention, and
  the container (I) is embodied as a storage container and contains a multiple of the amount of oxidizing agent preparation (A) that is necessary for an individual color-changing process.

In other words, a second subject of the present invention is a cosmetic product for oxidatively changing the color of keratin fibers, in particular human hair. The product includes:
  an oxidizing agent preparation (A), which is packaged in a container (I), wherein
  the oxidizing agent preparation (A) is present in the form of an oil-in-water emulsion (O/W emulsion), and includes:
(a1) an oil phase including one or more fat constituents (F),
(a2) a water phase,
(a3) hydrogen peroxide, and
(a4) at least one type of fine-grain particles (P) having a mean particle size of less than 200 μm (micrometers).
The container (I) is embodied as a storage container and contains a multiple of the amount of oxidizing agent preparation (A) that is necessary for an individual color-changing process.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly, it has now been found that the above-mentioned problem is solved in an excellent way by an oxidizing agent preparation which is present in the form of an (O/W) emulsion, comprises a water phase and also hydrogen peroxide in addition to an oil phase with fat constituents, and which is characterized by the content of at least one type of fine-grain particles having a mean particle size of less than 200 μm (micrometers).

Starches which comprise at least one carboxy-$(C_1$-$C_4)$ alkyl group are, for example, carboxymethyl starch, carboxyethyl starch and carboxypropyl starch. Carboxymethyl starch is used for example in the form of the trade product Covagel (carboxymethyl starch, sodium salt, potato starch used as starch source; INCI name: Sodium Carboxymethyl Starch) from the company Sensient/LCW.

The use of at least one type of fine-grain particles (P) formed of hydrophobically modified starches has proven to be very particularly suitable.

Hydrophobically modified starches are understood within the sense of the present invention to mean starches of which the polymer structure comprises at least one hydrophobic group, for example one or more $C_8$-$C_{30}$ alkyl groups and/or $C_8$-$C_{30}$ alkenyl groups. These hydrophobic groups (for example the alkyl groups) can be present for example linked to the starch molecule via an ester grouping, an ether grouping, or an amide group.

Again, the hydrophobically modified starches, in particular Aluminium Starch Octenylsuccinate, are very particularly preferably selected from the group of starches coated and/or modified as appropriate.

A very particularly preferred hydrophobically modified starch is "Aluminium Starch Octenyl Succinate", which is a starch modified with octenyl succinic acid anhydride and present in the form of its aluminum salt.

Aluminium Starch Octenyl Succinate has the CAS no. 9087-61-0 and is commercially available from the company Sensient, for example under the trade name Covafluid AMD.

A very particularly preferred Aluminium Starch Octenyl Succinate for example has a mean particle size of 16 μm (micrometers).

D50 (v)=16 μm (micrometers)

In a very particularly preferred embodiment an oxidizing agent preparation (A) according to the invention is characterized in that the oxidizing agent preparation (A) includes
(a4) at least one type of fine-grain particles (P) selected from the fine-grain, powdery solids, coated and/or modified as appropriate, from the group of silicon dioxide and/or starch.

In a very particularly preferred embodiment a product according to the invention is characterized in that the oxidizing agent preparation (A) includes
(a4) at least one type of fine-grain particles (P) selected from the fine-grain, powdery solids, coated and/or modified as appropriate, from the group of silicon dioxide and/or starch.

In an explicitly very particularly preferred embodiment an oxidizing agent preparation (A) according to the invention is characterized in that the oxidizing agent preparation (A) includes
(a4) at least one type of fine-grain particles (P) selected from fine-grain, powdery, pyrogenic silicon dioxide and/or fine-grain, powdery Silica Dimethyl Silylate and/or fine-grain, powdery Aluminium Starch Octenylsuccinate.

In an explicitly very particularly preferred embodiment a product according to the invention is characterized in that the oxidizing agent preparation (A) includes
(a4) at least one type of fine-grain particles (P) selected from fine-grain, powdery, pyrogenic silicon dioxide and/or fine-grain, powdery Silica Dimethyl Silylate and/or fine-grain, powdery Aluminium Starch Octenylsuccinate.

In a very particularly preferred embodiment, an oxidizing agent preparation (A) according to the invention is characterized in that the oxidizing agent preparation (A) includes
(a4) at least one type of fine-grain particles (P) having a mean particle size of 10 nm (nanometers) to 100 nm (nanometers) and selected from fine-grain, pyrogenic silicon dioxide.

In an explicitly very particularly preferred embodiment a product according to the invention is characterized in that the oxidizing agent preparation (A) includes
(a4) at least one type of fine-grain particles (P) having a mean particle size of 10 nm (nanometers) to 100 nm (nanometers) and selected from fine-grain, pyrogenic silicon dioxide.

In this regard, it could be found that a variation of the used amount of the microfine particle (P) also influences the viscosity of the oxidizing agent preparation (A). In order to set the oxidizing agent preparation (A) to the viscosity range optimal for mixing with the second component, the fine-grain particles (P) are therefore particularly preferably used in the oxidizing agent preparation (A) in specific amount ranges. It has proven to be particularly advantageous in this regard to use one or more types of fine-grain particles (P) in a total amount of from 0.05 to 5.0 wt. %, preferably from 0.05 to 2.5 wt. %, more preferably from 0.05 to 0.5 wt. %, even more preferably from 0.05 to 0.25 wt. %, and very particularly preferably from 0.05 to 0.1 wt. %. Here, the aforementioned amount values relate to the total amount of all fine-grain particles (P), which is set in relation to the total weight of the oxidizing agent preparation (A).

In this regard it has proven to be surprising in particular that a significant increase of the viscosity of the oxidizing agent preparation (A) was possible by use of just very small amounts of fine-grain particles (P). The viscosity of the oxidizing agent preparation could be significantly increased disproportionately for example by use of just 0.025 wt. % of fine-grain particles.

It has also been found that the addition of the fine-grain particles (P) had a positive effect on the mixing viscosity of the finished ready-to-use mixture. Even when mixing with a very highly viscous coloring cream (B) (or a highly viscous dye (B)), the viscosity of the ready-to-use mixture could be held in the desired viscosity range in a defined manner, without any unpredictable fluctuations and without any changes caused by the storage process.

In a very particularly preferred embodiment an oxidizing agent preparation (A) according to the invention is characterized in that the oxidizing agent preparation (A)—in relation to the total weight of the oxidizing agent preparation (A)—includes
(a4) one or more types of fine-grain particles (P) in a total amount of from 0.05 to 5.0 wt. %, preferably from 0.05 to 2.5 wt. %, more preferably from 0.05 to 0.5 wt. %, even more preferably from 0.05 to 0.25 wt. %, and very particularly preferably from 0.05 to 0.1 wt. %.

In a very particularly preferred embodiment a product according to the invention is characterized in that the oxidizing agent preparation (A)—in relation to the total weight of the oxidizing agent preparation (A)—includes
(a4) one or more types of fine-grain particles (P) in a total amount of from 0.05 to 5.0 wt. %, preferably from 0.05 to 2.5 wt. %, more preferably from 0.05 to 0.5 wt. %, even more preferably from 0.05 to 0.25 wt. %, and very particularly preferably from 0.05 to 0.1 wt. %.

The fine-grain particles (P) are characterized in accordance with the invention in that they have a mean particle size of less than 200 μm (micrometers). In this regard it has proven to be particularly advantageous to use particles having a mean particle size of from 10 nm (nanometers) to 180 μm (micrometers), preferably from 10 nm (nanometers) to 140 μm (micrometers), more preferably from 10 nm (nanometers) to 80 μm (micrometers) and very particularly preferably from 10 nm (nanometers) to 100 nm (nanometers). Here, the form in which the used particles are present (thin plates, rods, beads, etc.) is substantially irrelevant.

In a very particularly preferred embodiment an oxidizing agent preparation (A) according to the invention is characterized in that the oxidizing agent preparation (A) includes
(a4) at least one type of fine-grain particles (P) having a mean particle size of from 10 nm (nanometers) to 180 μm (micrometers), preferably from 10 nm (nanometers) to 140

µm (micrometers), more preferably from 10 nm (nanometers) to 80 µm (micrometers) and very particularly preferably from 10 nm (nanometers) to 100 nm (nanometers).

In a very particularly preferred embodiment a product according to the invention is characterized in that the oxidizing agent preparation (A) includes (a4) at least one type of fine-grain particles (P) having a mean particle size of from 10 nm (nanometers) to 180 µm (micrometers), preferably from 10 nm (nanometers) to 140 µm (micrometers), more preferably from 10 nm (nanometers) to 80 µm (micrometers) and very particularly preferably from 10 nm (nanometers) to 100 nm (nanometers).

The works leading to this invention have also shown that it is possible to produce the viscosity of the oxidizing agent preparation (A) exclusively by the addition of the fatty substances (F) and by the fine-grain particles (P). By use of the fine-grain particles (P), it is therefore also possible to dispense with the addition of thickening polymers.

Thickening polymers in the sense of the present invention are synthetic polymers which are soluble in the oxidizing agent preparation (A) or which form a gel in the oxidizing preparation agent (A). The thickening effect is produced by the dissolution or swelling (gel formation). The term thickening polymers thus explicitly does not mean any substances which are present in the dye (F) in the form of fine-grain particles.

If a polymer is present as a type of fine-grain particle having a mean particle size of less than 200 µm (micrometers) and is neither soluble nor swellable in the oxidizing agent preparation (A) (such that the polymer remains in the form of fine-grain particles in the oxidizing agent preparation (A)), it does not fall under the definition of a thickening polymer in the sense of the present invention.

By way of example, it is possible to dispense with synthetic polymers that are soluble in the oxidizing preparation agent (A) or swellable in the oxidizing preparation agent (A) and that act in a thickening way and can be obtained by polymerization of at least one unsaturated monomer. Corresponding monomers are: (meth)acrylic acid, (meth)acrylic acid ester, (meth)acrylamides, ethylene, propylene, styrene, vinylpyrrolidone or vinyl acetate, wherein the aforementioned monomers can also carry further substituents.

In an explicitly very particularly preferred embodiment an oxidizing agent preparation (A) according to the invention is characterized in that the oxidizing preparation agent (A) is substantially free from polymers obtained by polymerization of at least one monomer from the group of (meth)acrylic acid, (meth)acrylic acid esters, (meth)acrylamides, ethylene, propylene, styrene, vinylpyrrolidone and vinyl acetate.

In a very particularly preferred embodiment a product according to the invention is characterized in that the oxidizing preparation agent (A) is substantially free from polymers obtained by polymerization of at least one monomer from the group of (meth)acrylic acid, (meth)acrylic acid esters, (meth)acrylamides, ethylene, propylene, styrene, vinylpyrrolidone and vinyl acetate.

The fact that the oxidizing agent preparations (A) are substantially free from thickening polymers means in this regard that they do not include the thickening polymers in amounts that would lead to a thickening effect in the oxidizing agent preparation (A). The term "substantially free from thickening polymers" preferably means that the oxidizing agent preparation (A)—in relation to the total weight of the oxidizing agent preparation (A)—includes the thickening polymers in a total amount of at most 0.05 wt. %, preferably at most 0.01 wt. %, and very particularly preferably 0.001 wt. %.

In an explicitly very particularly preferred embodiment an oxidizing agent preparation (A) according to the invention is characterized in that, in the oxidizing agent preparation (A), the total content of polymers that can be obtained by polymerization of at least one monomer from the group of (meth)acrylic acid, (meth)acrylic acid esters, (meth)acrylamides, ethylene, propylene, styrene, vinylpyrrolidone and vinyl acetate is at most 0.05 wt. %. Here, the total content of the aforementioned polymers relates to the total weight of the oxidizing agent preparation (A).

In an explicitly very particularly preferred embodiment a product according to the invention is characterized in that, in the oxidizing agent preparation (A), the total content of polymers that can be obtained by polymerization of at least one monomer from the group of (meth)acrylic acid, (meth)acrylic acid esters, (meth)acrylamides, ethylene, propylene, styrene, vinylpyrrolidone and vinyl acetate is at most 0.05 wt. %. Here, the total content of the aforementioned polymers relates to the total weight of the oxidizing agent preparation (A).

The term "polymers" is understood to mean macromolecules having a molecular weight of at least 1,000 g/mol, preferably at least 2,500 g/mol, particularly preferably at least 5,000 g/mol, which consist of identical, repeating organic units. Polymers are produced by polymerization of one monomer type or by polymerization of various monomer types structurally different from each other. If the polymer is produced by polymerization of one monomer type, reference is made to homo-polymers. If structurally different monomer types are used in the polymerization, the resultant polymer is referred to as a copolymer.

The maximum molecular weight of the polymer is dependent on the degree of polymerization (number of polymerized monomers) and is also determined by the polymerization method. In the sense of the present invention it is preferred when the maximum molecular weight of the cationic polymer (d) is no more than $10^7$ g/mol, preferably no more than $10^6$ g/mol and particularly preferably no more than $10^5$ g/mol.

What is very particularly preferred is an oxidizing agent preparation (A) for oxidatively changing the color of keratin fibers, in particular human hair, which preparation is present in the form of an oil-in-water emulsion (O/W emulsion), comprising (a1) an oil phase including one or more fat constituents (F),
(a2) a water phase,
(a3) hydrogen peroxide,
(a4) at least one type of fine-grain particles (P) having a mean particle size of less than 200 µm (micrometers),
wherein the oxidizing agent preparation (A) has a viscosity of 7,000 to 12,000 mPas (22° C./Brookfield viscometer/spindle 4/4 rpm) and—in relation to the total weight of the oxidizing agent preparation (A)—includes one or more fat constituents (F) from the group of $C_{12}$-$C_{30}$ fatty alcohols in a total amount of from 0.5 to 2.0 wt. %. A corresponding product is also very particularly preferred.

What is very particularly preferred is an oxidizing agent preparation (A) for oxidatively changing the color of keratin fibers, in particular human hair, which preparation is present in the form of an oil-in-water emulsion (O/W emulsion), comprising (a1) an oil phase including one or more fat constituents (F),
(a2) a water phase,
(a3) hydrogen peroxide, (a4) at least one type of fine-grain particles (P) having a mean particle size of less than 200 μm (micrometers), selected from the fine-grain, powdery solids, coated and/or modified as appropriate, from the group of silicon dioxide and/or starch, wherein the oxidizing agent preparation (A) has a viscosity of 7,000 to 12,000 mPas (22° C./Brookfield viscometer/spindle 4/4 rpm) and—in relation to the total weight of the oxidizing agent preparation (A)—includes one or more fat constituents (F) from the group of $C_{12}$-$C_{30}$ fatty alcohols in a total amount of from 0.5 to 2.0 wt. %. A corresponding product is also very particularly preferred.

What is very particularly preferred is an oxidizing agent preparation (A) for oxidatively changing the color of keratin fibers, in particular human hair, which preparation is present in the form of an oil-in-water emulsion (O/W emulsion), comprising (a1) an oil phase including one or more fat constituents (F),
(a2) a water phase,
(a3) hydrogen peroxide,
(a4) at least one type of fine-grain particles (P) having a mean particle size of less than 200 μm (micrometers), selected from fine-grain, powdery, pyrogenic silicon dioxide and/or fine-grain, powdery Silica Dimethyl Silylate and/or fine-grain, powdery Aluminium Starch Octenylsuccinate, wherein the oxidizing agent preparation (A) has a viscosity of 7,000 to 12,000 mPas (22° C./Brookfield viscometer/spindle 4/4 rpm) and—in relation to the total weight of the oxidizing agent preparation (A)—includes one or more fat constituents (F) from the group of $C_{12}$-$C_{30}$ fatty alcohols in a total amount of from 0.5 to 2.0 wt. %. A corresponding product is very particularly preferred.

Further Ingredients in the Oxidizing Agent Preparation

In order to stabilize the hydrogen peroxide in the oxidizing agent preparation (A) it has also proven to be advantageous if the oxidizing agent preparation (A) includes at least one stabilizer or complexing agent. Conventional complexing agents and stabilizers that are preferred within the scope of the present invention are, for example, polyoxycarboxylic acids, polyamines, ethylenediaminetetraacetic acid (EDTA), N-hydroxyethylethylenediaminetriacetic acid, diethylenetriaminepentaacetic acid (DTPA), ethylenediaminedisuccinic acid (EDDS), hydroxyethyliminodiacetic acid, nitridodiacetic acid-3-propionic acid, isoserindiacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylenediaminedisuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), diaminoalkyldi-(sulfosuccinic acid) (DDS), ethylenedicysteic acid (EDC), ethylenediamine-N—N'-bis-(ortho-hydroxyphenyl)acetic acid (EDDHA), N-2-hydroxyethylamine-N,N-diacetic acid, glyceryliminodiacetic acid, iminodiacetic acid-N-2-hydroxypropylsulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, and salts and/or derivatives thereof, geminal diphosphonic acids such as 1-hydroxyethane-1,1-diphosphonic acid (HEDP), the higher homologs thereof with up to 8 carbon atoms, and also derivatives hereof including hydroxy or amino groups and 1-aminoethane-1,1-diphosphonic acid, the higher homologs thereof with up to 8 carbon atoms, and also derivatives including hydroxy or amino groups, amino-phosphonic acids such as ethylenediamine tetra(methylene phosphonic acid) (EDTMP), diethylenetriamine penta(methylene phosphonic acid) (DTPMP) and higher homologs thereof, or nitrilotris(methylene phosphonic acid), phosphonopolycarboxylic acids such as 2-phosphonobutane-1,2,4-tricarboxylic acid, cyclodextrins, and alkali stannates (sodium stannate), alkalipyrophosphates (tetrasodiumpyrophosphate, disodiumpyrophosphate), alkaliphosphates (sodium phosphate), and phosphoric acid and salts thereof.

Multi-Component Packaging Unit

For the oxidative coloring of keratin fibers, the oxidizing agent preparation (A) is mixed with a dye (B) just before use. For mixing, an oxidizing agent preparation (A) for example can be transferred from a container (I) in which it is packaged into the container (II), wherein the dye (B) is already disposed in the container (II). It is also possible for the dye (B) to be transferred from the container (II) in which it was packaged into the container (I), wherein the oxidizing agent preparation (A) is already disposed in the container (I). The mixing can be performed in both cases for example by shaking the two preparations.

Alternatively, it is also possible to transfer both the oxidizing agent preparation (A) from container (I) and the dye (B) from container (II) into a third container, in which both preparations are then shaken, stirred, or otherwise combined.

The container (I) and/or (II) can be, for example, a bottle, a tube, a can or a sachet. The container (I) is very particularly preferably a storage container.

The amounts in which the oxidizing agent preparation (A) and the dye (B) are mixed with one another can be selected depending on the hair length or color intensity. It is usual to mix the oxidizing agent preparation (A) and the dye (B) with one another in a ratio by weight of 1:5 to 5:1. For reasons of user comfort, a mixing ratio of 1:3 to 3:1, preferably from 2:1 to 2:1, and very particularly preferably of approximately 1:1 is selected. With a mixing ratio of 2:1, the user for example mixes 200 g of oxidizing agent preparation (A) and 100 g of dye/coloring cream (B).

A third subject of the present invention is a multi-component packaging unit (kit-of-parts) for oxidatively changing the color of keratin fibers, in particular human hair, comprising, packaged separately from one another,
 a container (I) containing a cosmetic agent (A) and
 a container (II) containing a cosmetic agent (B),
wherein
 the agent (A) in container (I) is an oxidizing agent preparation (A) as has been disclosed in the description of the first subject of the invention, and
 the agent (B) is a dye including at least one oxidation dye precursor and/or at least one direct dye.

Oxidation Dye Precursor and/or Direct Dyes

In the multi-component packaging unit (kit-of-parts), the dye (B) includes at least one oxidation dye precursor and/or at least one direct dye.

Oxidation dye precursors can be divided into developers and couplers, wherein, on account of their greater sensitivity to oxygen, the developers are usually used in the form of their physiologically acceptable salts (for example in the form of their hydrochlorides, hydrobromides, hydrogen sulfates or sulfates).

Coupler components alone, within the scope of oxidative dyeing, do not produce a significant coloring, and always require the presence of developer components. Since couplers are not as sensitive to oxygen as developers, they can also be used in the preparation in the form of their salts, but are often also used in free form (i.e. not in salt form).

Preferred physiologically acceptable salts of developers are, for example, p-phenylenediamine×H$_2$SO$_4$, p-phenylenediamine×2HCl, p-toluenediamine×H$_2$SO$_4$, p-toluenediamine×2HCl, 2-(2-hydroxyethyl)-p-phenylenediamine×H$_2$SO$_4$, 2-(2-hydroxyethyl)-p-phenylenediamine×2HCl, 2-(1,2-dihydroxyethyl)-p-phenylenediamine×H$_2$SO$_4$, 2-(1,2-dihydroxyethyl)-p-phenylenediamine×2HCl, N,N-bis-(2-hydroxyethyl)-p-phenylenediamine×H$_2$SO$_4$, N,N-bis-(2-hydroxyethyl)-p-phenylenediamine×2HCl, 2-methoxymethyl-p-phenylenediamine×H$_2$SO$_4$, 2-methoxymethyl-p-phenylenediamine×2 HCl, N-(4-amino-3-methylphenyl)-N-[3-(1H-imidazol-1-yl)propyl]amine×H$_2$SO$_4$, N-(4-amino-3-methylphenyl)-N-[3-(1H-imidazol-1-yl)propyl]amine×2HCl, N-(4-amino-3-methylphenyl)-N-[3-(1H-imidazol-1-yl)propyl]amine×3 HCl, bis-(2-hydroxy-5-aminophenyl)methane×H$_2$SO$_4$, bis-(2-hydroxy-5-aminophenyl)methane×2HCl, 4,5-diamino-1-(2-hydroxyethyl)-1H-pyrazole×H$_2$SO$_4$, 4,5-diamino-1-(2-hydroxyethyl)-1H-pyrazole×2HCl, 2,4,5,6-tetraaminopyrimidine×H$_2$SO$_4$, 2,4,5,6-tetraaminopyrimidine×2H$_2$SO$_4$, 2,4,5,6-tetraaminopyrimidine×2HCl, 2,4,5,6-tetraaminopyrimidine×3 HCl, 2,4,5,6-tetraaminopyrimidine×4 HCl, 4-hydroxy-2,5,6-triaminopyrimidine×H$_2$SO$_4$, 4-hydroxy-2,5,6-triaminopyrimidine×2HCl, 2-hydroxy-4,5,6-triaminopyrimidine×H$_2$SO$_4$, 2-hydroxy-4,5,6-triaminopyrimidine×2HCl, 2-hydroxy-4,5,6-triaminopyrimidine×3 HCl.

Depending on the desired color result, oxidation dye precursors of the developer type and of the coupler type are used in different quantity proportions in the dye.

If dyeing in a blond shade is desired, the use of oxidation dye precursors in a total amount of less than 1.0 wt. % or even less than 0.5 wt. % is usually sufficient.

If, however, the user wishes to color in a very dark shade, for example in a dark brown shade or in a black shade, this necessitates the use of oxidation dye precursors in the total amount of at least 2.0 wt. %, often 3.0 wt. %, and in the case of particularly dark shades (black) even above 4.5 wt. % (in relation to the total weight of the dye (B)).

Oxidation dye precursors of the developer type can be included as the sole color-changing compounds in the agent according to the invention. However, it is preferred in accordance with the invention when the dye (B) additionally includes at least one oxidation dye precursor of the coupler type (referred to as a coupler for short).

Coupler components alone, within the scope of oxidative dyeing, do not produce a significant coloring, and always require the presence of developer components. Coupler components in the sense of the invention allow at least one substitution of a chemical group of the coupler by the oxidized form of the developer component. Here, covalent bonds are formed between coupler and developer component.

At least one compound from one of the following classes is preferably selected as a suitable coupler component in accordance with the invention:
  m-diaminobenzene and/or derivatives thereof,
  o-diaminobenzene and/or derivatives thereof,
  o-aminophenol derivatives, such as o-aminophenol,
  naphthalene derivatives with at least one hydroxy group,
  di- or trihydroxybenzene and/or derivatives thereof,
  pyridine derivatives,
  pyrimidine derivatives,
  monohydroxyindole derivatives and/or monoaminoindole derivatives,
  monohydroxyindoline derivatives and/or monoaminoindoline derivatives,
  pyrazolone derivatives, such as 1-phenyl-3-methylpyrazol-5-one,
  morpholine derivatives, such as 6-hydroxybenzomorpholine or 6-aminobenzomorpholine,
  quinoxaline derivatives, such as 6-methyl-1,2,3,4-tetrahydroquinoxaline.

Mixtures of two or more compounds from one or more of these classes are also suitable in accordance with the invention within the scope of this embodiment.

In a further embodiment, a dye (B) according to the invention is characterized in that it includes at least one oxidation dye precursor of the coupler type which is selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2-hydroxyethylamino)benzene, 1,3-bis(2,4-diaminophenyl)propane, 2,6-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-on, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline and the physiologcally acceptable salts thereof.

The oxidation dye precursors can be included in a total amount of from 0.001 to 10 wt. % in the dye (B) according to the invention.

In addition to the oxidation dye precursors or instead of these, the dyes (B) according to the invention can include at least one direct dye. These are dyes which are drawn directly onto the hair and which do not require an oxidative process in order to form the color. Direct dyes are usually nitrophenylenediamines, nitroaminophenols, azo dyes, anthraquinones, triarylmethane dyes, or indophenols.

Direct dyes can be divided into anionic, cationic, and non-ionic direct dyes.

In particular, non-ionic nitro dyes and quinone dyes and neutral azo dyes are suitable as non-ionic direct dyes. Preferred non-ionic direct dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Anionic direct dyes carry at least one negative charge and are also referred to in the literature as acid dyes. Preferred anionic direct dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Cationic dyes are characterized by the presence of at least one positive charge. In the English literature, cationic dyes are also referred to as "basic dyes". Preferred cationic direct dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31, and Basic Red 51.

The direct dyes are included in the dye (B) according to the invention in a total amount of from 0.001 to 10 wt. %.

In order to produce the finished ready-to-use mixture, the oxidizing agent preparation (A) according to the invention is mixed with the dye (B). The oxidizing agent preparation (A) is present in accordance with the invention in the form of an (O/W) emulsion, and the dye (B) is preferably also used in emulsion form, particularly preferably in the form of an (O/W) emulsion.

In order to also ensure an optimal and quick miscibility of the preparations (A) and (B) in addition to good properties for the intended use, both preparations (A) and (B) are preferably set to a specific viscosity range.

The viscosity of the dye (A) can be determined in particular by the interaction of the amount of fat constituents (F) and the amount of fine-grain particles (P).

Since the oxidizing agent preparation (A) as described beforehand is preferably set to low viscosity ranges, it has proven to be advantageous if the dye (B) is set to a higher viscosity than the oxidizing agent preparation (A).

Within this embodiment the thin oxidizing agent preparation (A) can be provided for example in a 1,000 ml or 1,500 ml storage bottle. For the mixing of (A) with (B), a portion of (A) and the coloring cream (B) are transferred for example into a mixing bowl. If both preparations (A) and (B) have been set to their optimal viscosity ranges, this ensures a very quick miscibility and the production of a homogenous, stable and rheologically optimized ready-to-use mixture. For the aforementioned reasons it is very particularly preferred if the dye (B) has a viscosity of from 10,000 to 50,000 mPas, preferably from 10,000 to 40,000 mPas, and particularly preferably from 15,000 to 30,000 mPas (22° C./Brookfield viscometer/spindle 4/4 rpm).

In an explicitly very particularly preferred embodiment a multi-component packaging unit according to claim 14 is characterized in that the dye (B) has a viscosity of from 10,000 to 50,000 mPas, preferably from 10,000 to 40,000 mPas, and particularly preferably from 15,000 to 30,000 mPas (22° C./Brookfield viscometer/spindle 4/4 rpm).

The ready-to-use mixture produced by the mixing of the preparations (A) and (B) also preferably meets certain specification requirements in view of the viscosity of said preparations.

The oxidizing agent preparation (A) and the dye (B) can be mixed with one another for example in a ratio by weight of from 1:5 to 5:1. A mixing ratio of from 1:3 to 3:1, more preferably from 2:1 to 2:1, and very particularly preferably of approximately 1:1 is preferably selected.

If, for example, a mixing ratio of 1:1 is selected (mixing of 100 g oxidizing agent preparation (A) and 100 g dye (B)), the viscosity thus lies very particularly preferably in the range of from 10,000 to 50,000 mPas, preferably from 12,000 to 45,000 mPas, more preferably from 12,000 to 40,000 mPas, and very particularly preferably from 12,000 to 38,000 mPas (22° C./Brookfield viscometer/spindle 4/4 rpm).

In an explicitly very particularly preferred embodiment a multi-component packaging unit according to the invention is characterized in that the mixture of the oxidizing agent preparation (A) and the dye (B), when (A) and (B) are mixed at a ratio by weight of 1:1, has a viscosity of from 10,000 to 50,000 mPas, preferably from 12,000 to 45,000 mPas, more preferably from 12,000 to 40,000 mPas, and very particularly preferably from 12,000 to 38,000 mPas (22° C./Brookfield viscometer/spindle 4/4 rpm).

Further Ingredients

The oxidizing agent preparation (A) and/or the dye (B) can additionally also include one or more surfactants.

Surfactants that are preferred in accordance with the invention are selected from the group of anionic, cationic, amphoteric and/or non-ionic surfactants or from mixtures thereof.

All anionic surface-active substances suitable for use on the human body or on technical surfaces are suitable as anionic surfactants in the compositions according to the invention. These substances are characterized by anionic groups that impart a water-soluble effect, such as a carboxylate, sulfate, sulfonate, or phosphate group and a lipophilic alkyl group having approximately 8 to 30 C atoms. In addition, glycol- or polyglycolether groups, ester, ether and amide groups, and hydroxyl groups can additionally be included in the molecule. Examples of suitable foaming anionic surfactants are, in each case in the form of the sodium, potassium and ammonium and also the mono-, di- and trialklanol ammonium salts having 2 to 4 carbon atoms in the alkanol group, acyl glutamates of formula (I),

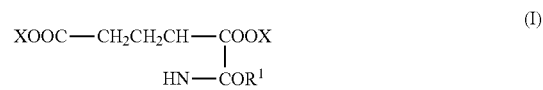

in which $R^1CO$ stands for a linear or branched acyl group having 6 to 22 carbon atoms and 0, 1, 2 or 3 double bonds and X stands for hydrogen, an alkali and/or alkaline earth metal, ammonium, alkylammonium, alkanol ammonium or glucammonium, for example acyl glutamates which derive from fatty acids having 6 to 22, preferably 12 to 18 carbon atoms, such as $C_{12/14}$ or $C_{12/18}$ coconut fatty acid, lauric acid, myristic acid, palmitic acid and/or stearic acid, in particular sodium-N-cocoyl-L-glutamate and sodium-N-stearoyl-L-glutamate, esters of a hydroxy-substituted di- or tricarboxylic acid of general formula (II),

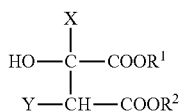

(II)

in which X=H or is a —CH$_2$COOR group, Y=H or is —OH on the condition that Y=H when X=—CH$_2$COOR, R, R$^1$ and R$^2$ independently of one another mean a hydrogen atom, an alkali or alkaline earth metal cation, an ammonium group, the cation of an ammonium-organic base, or a group Z which originates from a polyhdroxylated organic compound, which are selected from the group of etherified (C$_6$-C$_{18}$) alkylpolysaccharides having 1 to 6 monomer saccharide units and/or the etherified aliphatic (C$_6$-C$_{16}$) hydroxyalkylpolyols having 2 to 16 hydroxyl groups, on the provision that at least one of the groups R, R$^1$ or R$^2$ is a group Z, esters of the sulfosuccinic acid salt of general formula (III),

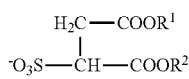

(III)

in which R$^1$ and R$^2$ independently of one another mean a hydrogen atom, an alkali or alkaline earth metal cation, an ammonium group, the cation of an ammonium-organic base, or a group Z which originates from a polyhydroxylated organic compound, which are selected from the group of etherified (C$_6$-C$_{18}$) alkylpolysaccharides having 1 to 6 monomer saccharide units and/or the etherified aliphatic (C$_6$-C$_{16}$) hydroxyalkylpolyols having 2 to 16 hydroxyl groups, on the provision that at least one of the groups R$^1$ or R$^2$ is a group Z, sulfosuccinic acid mono and dialkyl esters having 8 to 24 C atoms in the alkyl group and sulfosuccinic acid monoalkylpolyoxyethyl esters having 8 to 24 C atoms in the alkyl group and 1 to 6 ethoxy groups, esters of tartaric acid and citric acid with alcohols, which are addition products of approximately 2-15 molecules of ethylene oxide and/or propylene oxide with fatty alcohols having 8 to 22 C atoms, linear and branched fatty acids having 8 to 30 C atoms (soaps), ethercarboxylic acids of formula R—O—(CH$_2$—CH$_2$O)$_x$—CH$_2$—COOH, in which R is a linear alkyl group having 8 to 30 C atoms and x=0 or 1 to 16, acylsarcosinates with a linear or branched acyl group having 6 to 22 carbon atoms and 0, 1, 2 or 3 double bonds, acyl taurates with a linear or branched acyl group having 6 to 22 carbon atoms and 0, 1, 2 or 3 double bonds, acylisethionates having a linear or branched acyl group having 6 to 22 carbon atoms and 0, 1, 2 or 3 double bonds, linear alkanesulfonates having 8 to 24 C atoms, linear alpha-olefin sulfonates having 8 to 24 C atoms, alpha-sulfofatty acid methyl esters of fatty acids having 8 to 30 C atoms, alkyl sulfates and alkyl polyglycol ether sulfates of formula R—O(CH$_2$—CH$_2$O)$_z$—SO$_3$X, in which R is a preferably linear alkyl group having 8 to 30 C atoms, particularly preferably having 8-18 C atoms, z=0 or 1 to 12, particularly preferably 3, and X is a sodium, potassium, magnesium, zinc, ammonium ion or a monoalcohol, dialkanol, or trialkanol ammonium ion having 2 to 4 carbon atoms in the alkanol group, wherein a particularly preferred example is zinc cocoyl ether sulfate with a degree of ethoxylation of z=3, mixtures of surface-active hydroxysulfonates according to DE-A-37 25 030, sulfated hydroxyalkyl polyethylene and/or hydroxyalkylene propylene glycol ethers according to DE 3723354, sulfonates of unsaturated fatty acids having 8 to 24 C atoms and 1 to 6 double bonds according to DE 3926344, alkyl and/or alkenyl ether phosphates of formula (IV),

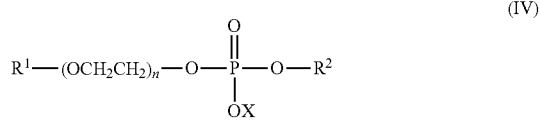

(IV)

in which R$^1$ preferably stands for an aliphatic hydrocarbon group having 8 to 30 carbon atoms, R$^2$ stands for hydrogen, a group (CH$_2$CH$_2$O)$_n$R$^1$ or X, n stands for numbers from 1 to 10, and X stands for hydrogen, an alkali or alkaline earth metal or NR$^3$R$^4$R$^5$R$^6$, with R$^3$ to R$^6$ independently of one another standing for a C$_1$ to C$_4$ hydrocarbon group, sulfated fatty acid alkylene glycol esters of formula R$^7$CO(AlkO)$_n$SO$_3$M, in which R$^7$CO— stands for a linear or branched, aliphatic, saturated and/or unsaturated acyl group having 6 to 22 C atoms, Alk stands for CH$_2$CH$_2$, CHCH$_3$CH$_2$ and/or CH$_2$CHCH$_3$, n stands for numbers from 0.5 to 5, and M stands for a cation, as are described in DE 19736906, monoglyceride sulfates and monoglyceride ether sulfates of formula (V),

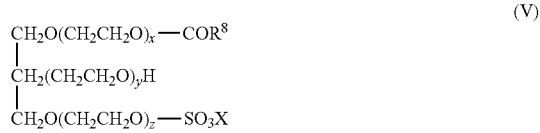

(V)

in which R$^8$CO stands for a linear or branched acyl group having 6 to 22 carbon atoms, x, y and z in total stand for 0 or for numbers from 1 to 30, preferably 2 to 10, and X stands for an alkali or alkaline earth metal. Typical examples for monoglyceride (ether) sulfates suitable in the sense of the invention are the reaction products of lauric acid monoglyceride, coconut fatty acid monoglyceride, palmitic acid monoglyceride, stearic acid monoglyceride, oleic acid monoglyceride, and tallow fatty acid monoglyceride and also the ethylene oxide adducts thereof with sulfur trioxide or chlorosulfonic acid in the form of the sodium salts thereof. Monoglyceride sulfates of formula (V) in which R$^8$CO stands for a linear acyl group having 8 to 18 carbon atoms are preferably used.

All cationic surface-active substances suitable for use on the human body or on technical surfaces are suitable as cationic surfactants in the compositions according to the invention.

Cationic surfactants are characterized in cosmetic fields of application in that they contribute to a significantly improved cosmetic appearance of skin and hair, similarly to amphoteric and zwitterionic surfactants. The cationic charge ensures a good binding to the more likely negatively charged surfaces, in particular of damaged hair or stressed skin. Active substances that are more likely hydrophobic in structure can in turn adhere to the long fat residues of these molecular structures. On the whole, an increased deposition of nourishing substances on the surface of skin and hair is produced as a result. The hair can be better combed, for example both in the dry and wet state, can be styled more easily, and exhibits greater shine and also has a more pleasant feel.

Cationic surfactants generally derive from ammonium ions and have a structure $(NR^1R^2R^3R^4)^+$ with an accordingly negatively charged counterion. Cationic ammonium compounds of this type are best known to a person skilled in the art. Further cationic surfactants are for example the esterquats or the imidazolium compounds. Cationic surfactants of the type constituted by the quaternary ammonium compounds, the esterquats, the imidazolines, and the amidoamines can be used with particular preference in accordance with the invention. Preferred quaternary ammonium compounds are ammonium halides, in particular chlorides and bromides, such as alkyl trimethyl ammonium chlorides, dialkyl dimethyl ammonium chlorides, and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, and the imidazolium compounds known under the INCI names Quaternium-27 and Quaternium-83. The long alkyl chains of the above-mentioned surfactants preferably have 8 to 30 carbon atoms. Typical examples of cationic surfactants are quaternary ammonium compounds and esterquats, in particular quaternized fatty acid trialkanol amine ester salts.

Cationic compounds with behenyl residues, in particular the substances known under the name behentrimonium chloride or bromide (Docosanyltrimethylammonium Chloride or Bromide) can be used with particular preference in accordance with the invention. Other preferred QAVs have at least two behenyl residues. These substances are commercially obtainable for example under the names Genamin® KDMP (Clariant).

Esterquats are known substances that include both at least one ester function and at least one quaternary ammonium group as structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are sold for example under the trademarks Stepantex®, Dehyquart® and Armocare®. The products Armocare® VGH-70, an N,N-bis(2-palmitoyloxyethyl)dimethylammonium chloride, and Dehyquart® F-75, Dehyquart® C-4046, Dehyquart® L80 and Dehyquart® AU-35 are examples of such esterquats.

Potential amphoteric/zwitterionic surfactants are surface-active compounds which are suitable for use on the human body or on technical surfaces and which carry at least one quaternary ammonium group and at least one —COO⁻ or —SO₃⁻ group in the molecule. Particularly suitable amphoteric surfactants are what are known as the betaines, such as N-alkyl-N,N-dimethylammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines including in each case 8 to 18 carbon atoms in the alkyl or acyl group and cocoacylaminoethyl hydroxyethyl carboxymethyl glycinate. A preferred zwitterionic surfactant is the fatty acid amide derivative known under the INCI name Cocamidopropyl Betaine.

All non-ionic surfactants which are suitable for use on the human body or on technical surfaces can also be considered as surface-active compounds that can be used in accordance with the invention and for example include, but are not limited to the following:

Non-ionic surfactants within the scope of the invention are alkoxylates, such as polyglycol ethers, fatty alcohol polyglycol ethers, alkylphenol polyglycol ethers, end group-capped polyglycol ethers, mixed ethers and hydroxy mixed ethers and fatty acid polyglycol esters. Ethylene oxide/propylene oxide block polymers, fatty acid alkanolamides and fatty acid polyglycol ethers can likewise be used. Important classes of non-ionic surfactants according to the invention are also the amine oxides and the sugar surfactants, in particular the alkyl polyglucosides.

Fatty alcohol polyglycol ethers are to be understood in accordance with the invention to mean unbranched or branched, saturated or unsaturated $C_{10-22}$ alcohols alkoxylated with ethylene oxide (EO) and/or propylene oxide (PO) with a degree of alkoxylation of up to 30, preferably ethoxylated $C_{10-18}$ fatty alcohols with a degree of ethoxylation of less than 30, preferably with a degree of ethoxylation of from 1 to 20, in particular from 1 to 12, particularly preferably from 1 to 8, extremely preferably from 2 to 5, for example $C_{12-14}$ fatty alcohol ethoxylates with 2, 3 or 4 EO or a mixture of the $C_{12-14}$ fatty alcohol ethoxylates with 3 and 4 EO in a ratio by weight of 1 to 1 or isotridecyl alcohol ethoxylate with 5, 8 or 12 EO.

Amine Oxides

Amine oxides that are suitable in accordance with the invention include alkyl amine oxides, in particular alkyl dimethyl amine oxides, alkyl amido amine oxides, and alkoxy alkyl amine oxides. Preferred amine oxides satisfy formula VII,

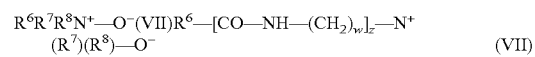

$$R^6R^7R^8N^+—O^-(VII)R^6—[CO—NH—(CH_2)_w]_z—N^+(R^7)(R^8)—O^- \quad (VII)$$

in which $R^6$ is a saturated or unsaturated $C_{6-22}$ alkyl group, preferably a $C_{8-18}$ alkyl group, in particular a saturated $C_{10-16}$ alkyl group, for example a saturated $C_{12-14}$ alkyl group, which is bound to the nitrogen atom N in the alkyl amido amine oxides via a carbonyl amido alkylene group —CO—NH—(CH$_2$)$_z$— and in the alkoxy alkyl amine oxides via an oxaalkylene group —O—(CH$_2$)$_z$—, wherein z in each case stands for a number from 1 to 10, preferably 2 to 5, in particular 3, $R^7$, $R^8$ independently of one another are a $C_{1-4}$ alkyl group, optionally hydroxy-substituted, such as a hydroxyethyl group, in particular a methyl group.

Examples of suitable amine oxides are the following compounds as named in accordance with the INCI: Almond amidopropylamine Oxide, Babassuamidopropylamine Oxide, Behenamine Oxide, Cocamidopropyl Amine Oxide, Cocamidopropylamine Oxide, Cocamine Oxide, Coco-Morpholine Oxide, Decylamine Oxide, Decyltetradecylamine Oxide, Diaminopyrimidine Oxide, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Hydrogenated Palm Kernel Amine Oxide, Hydrogenated Tallowamine Oxide, hydroxyethyl hydroxypropyl C12-15 Alkoxypropylamine Oxide, Isostearamidopropylamine Oxide, Isostearamidopropyl Morpholine Oxide, Lauramidopropylamine Oxide, Lauramine Oxide, Methyl Morpholine Oxide, Milkamidopropyl Amine Oxide, Minkamidopropylamine Oxide, Myristamidopropylamine Oxide, Myristamine Oxide, Myristyl/Cetyl Amine Oxide, Oleamidopropylamine Oxide, Oleamine Oxide, Olivamidopropylamine Oxide, Palmitamidopropylamine Oxide, Palmitamine Oxide, PEG-3 Lauramine Oxide, Potassium Dihydroxyethyl Cocamine Oxide Phosphate, Potassium Trisphosphonomethylamine Oxide, Sesamidopropylamine Oxide, Soyamidopropylamine Oxide, Stearamidopropylamine Oxide, Stearamine Oxide, Tallowamidopropylamine Oxide, Tallowamine Oxide, Undecylenamidopropylamine Oxide and Wheat Germamidopropylamine Oxide. A preferred amine oxide is for example Cocamidopropylamine Oxide.

Sugar Surfactants

Sugar surfactants are known surface-active compounds, which for example include the sugar surfactant classes of the alkylglucose esters, aldobionamides, gluconamides (sugar acid amides), glycerol amides, glycerol glycolipids, polyhydroxy fatty acid amide sugar surfactants (sugar amides) and alkyl polyglycosides. Within the scope of the teaching according to the invention, preferred sugar surfactants are the alkyl polyglycosides and the sugar amides and also derivatives thereof, in particular the ethers and esters thereof. The ethers are the products of the reaction of one or more, preferably one, sugar hydroxy group with a compound including one or more hydroxy groups, for example $C_{1-22}$ alcohols or glycols, such as ethylene and/or propylene glycol, wherein the sugar hydroxy group can also carry polyethylene glycol and/or polypropylene glycol groups. The esters are the reaction products of one or more, preferably one, sugar hydroxy group with a carboxylic acid, in particular a $C_{6-22}$ fatty acid.

Alkyl Polyglycosides

The alkyl polyglycosides (APGs) are particularly preferred sugar surfactants within the scope of the teaching according to the invention and preferably satisfy the general formula $RO(AO)_a[G]_x$, in which R stands for a linear or branched, saturated or unsaturated alkyl group having 6 to 22, preferably 6 to 18, in particular 8 to 16, particularly preferably 8 to 14 carbon atoms, [G] stands for a glycosidically linked sugar residue, and x stands for a number from 1 to 10 and AO stands for an alkylene oxy group, for example an ethylene oxy group or propylene oxy group, and a stands for the mean degree of alkoxylation from 0 to 20. Here, the group $(AO)_a$ can also include different alkylene oxy units, for example ethylene oxy or propylene oxy units, wherein a is then the mean overall degree of alkoxylation, i.e. the sum of degree of ethoxylation and degree of propoxylation. Unless otherwise stated hereinafter, the alkyl groups $R^1$ of the APGs are linear unsaturated groups with the specified number of carbon atoms.

APGs are non-ionic surfactants and constitute known substances which can be obtained in accordance with the relevant methods within the field of preparative organic chemistry. The index number x indicates the degree of oligomerization (DP degree), i.e. the distribution of mono- and oligoglycosides, and stands for a number between 1 and 0, Whereas x in a given compound always has to be a whole number, and here can assume the values x=1 to 6, the value x for a specific alkyl glycoside is an analytically determined mathematical variable, which is usually a fractional number. Alkyl glycosides having a mean degree of oligomerization x of from 1.1 to 3.0 are preferably used. With regard to the use, alkyl glycosides of which the degree of oligomerization is less than 1.7 and in particular is between 1.2 and 1.6 are preferred. Xylose, but in particular glucose, is preferably used as glycosidic sugar.

The alkyl or alkenyl group R preferably derives from lauryl alcohol, myristyl alcohol, cetyl alcohol, palmoleyl alcohol, stearyl alcohol, isostearyl alcohol or oleyl alcohol. Further examples include elaidyl alcohol, petroselinyl alcohol, arachidyl alcohol, gadoleyl alcohol, behenyl alcohol, erucyl alcohol and the technical mixtures thereof.

Particularly preferred APGs are non-alkoxylated (a=0) and satisfy formula $RO[G]_x$, in which R, as before, stands for a linear or branched, saturated or unsaturated alkyl group having 4 to 22 carbon atoms, [G] stands for a glycosidically linked sugar residue, preferably a glucose residue, and x stands for a number from 1 to 10, preferably 1.1 to 3, in particular 1.2 to 1.6. Preferred alkyl polyglycosides are, for example, preferably $C_{8-10}$ and a $C_{12-14}$ alkyl polyglucoside with a DP degree of 1.4 or 1.5, in particular $C_{8-10}$ alkyl-1,5-glucoside and $C_{12-14}$ alkyl-1,4-glucoside.

In a further embodiment of the invention the proportion of one or more surfactants, if used—in relation to the total amount of the preparations (A) and/or (B)—is 0.5 to 20 wt. %, particularly preferably 0.6 to 10 wt. %, more preferably 0.7 to 8 wt. %, and in particular 0.8 to 6 wt. %, 0.9 to 4 wt. % or 1 to 3 wt. %.

The agents according to the invention can also include further active substances, for example structuring substances such as glucose, maleic acid and lactic acid, fatty substances (in preparation (B)), alkalizing agents such as ammonia, monoethanol amine, potassium hydroxide and sodium hydroxide; hair-conditioning compounds such as phospholipids, for example lecithin and cephalin; perfume oils, fiber structure-improving active substances, in particular mono-, di- and oligosaccharides, such as glucose, galactose, fructose, fruit sugars and lactose; dyes for colouring the agent; anti-dandruff active substances such as piroctone olamine, zinc omadine and climbazole; amino acids and oligopeptides; animal-based and/or plant-based protein hydrolysates and protein hydrolysates in the form of their fatty acid condensation products or optionally anionically or cationically modified derivatives; vegetable oils; light stabilisers and UV blockers; active substances such as panthenol, pantothenic acid, pantolactone, allantoin, pyrrolidone carboxylic acids and salts thereof, and bisabolol; polyphenols, in particular hydroxycinnamic acids, 6,7-dihydroxycoumarin, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; swelling and penetrating substances such as glycerol, propylene glycol monoethyl ether, carbonates, hydrogen carbonates, guanidines, ureas and primary, secondary and tertiary phosphates; turbidity agents such as latex, styrene/PVP and styrene/acrylamide copolymers; pearlescent agents such as ethylene glycol mono- and distearate and PEG-3 distearate; pigments and also propellants such as propane-butane mixtures, $N_2O$, dimethyl ether, $CO_2$ and air.

The additional active substances and auxiliaries are preferably used in amounts of in each case 0.0001 to 10 wt. %, in particular from 0.0005 to 5 wt. %, in relation to the total weight of the oxidizing agent preparation (A) and the dye (B).

The oxidizing agent preparations (A) according to the invention are preferably produced in accordance with a specific method, as a result of which it is ensured that the solid particles are arranged at the interface between both oil phase and water phase and form there the desired mechanical barrier against the amalgamation of the droplets.

A further subject of the present invention is a method for producing an oxidizing agent preparation (A) according to the first subject of the invention, comprising the following steps
(I) heating (a1) one or more fat constituents (F) to a temperature above the melting point of the fat constituents (F),
(II) adding water (a2),
(III) cooling the mixture to a temperature below the melting point of the fat constituents (F),
(IV) adding (a3) hydrogen peroxide,
(V) adding (a4) at least one type of microfine particles (P) having a mean particle size of less than 200 μm (micrometers),
characterized in that step (V) is carried out after step (III).

What is particularly preferred is a method according to the invention that is characterized by steps (I), followed by step (II), followed by step (III), followed by step (IV), followed by step (V).

What is particularly preferred is a method according to the invention that is characterized by the steps (I), followed by step (II), followed by step (III), followed by step (V), followed by step (IV).

Steps (I) to (V) are particularly preferably carried out under stirring.

That which has been said in relation to the oxidizing agent preparation (A) and in relation the product according to the invention applies, mutatis mutandis, with regard to the preferred embodiments of the multi-component packaging unit according to the invention.

That which has been said in relation to the oxidizing agent preparation (A) and in relation the product according to the invention applies, mutatis mutandis, with regard to the preferred embodiments of the method according to the invention.

Examples

1. Oxidizing Agent Preparation (A)
The following oxidizing agent preparations were produced (all values in wt. %).
AV=oxidizing agent preparation, comparison
AE=oxidizing agent preparation, according to the invention

| | Oxidizing agent preparation (A) | | | |
|---|---|---|---|---|
| | (AV) | (AE1) | (AE2) | (AE3) |
| EDTA (disodium salt) | 0.15 | 0.15 | 0.15 | 0.15 |
| Disodium pyrophosphate | 0.30 | 0.30 | 0.30 | 0.30 |
| Sodium benzoate | 0.04 | 0.04 | 0.04 | 0.04 |
| Citric acid | 0.01 | 0.01 | 0.01 | 0.01 |
| Phosphoric acid | 0.04 | 0.04 | 0.04 | 0.04 |
| Sodium cetearyl sulfate | 0.16 | 0.16 | 0.16 | 0.16 |
| Cetearyl alcohol | 1.63 | 1.63 | 1.63 | 1.63 |
| PEG-40 Castor Oil | 0.32 | 0.32 | 0.32 | 0.32 |
| Hydrogen peroxide | 3.00 | 3.00 | 3.00 | 3.00 |
| Pyrogenic, amorphous, silicon dioxide, mean particle size 12 nm (Aerosil 200) | — | 0.0125 | 0.025 | 0.25 |
| Water (dist.) | to 100 | to 100 | to 100 | to 100 |

The fatty alcohols were first melted under stirring at 80° C., then the surfactants pre-dissolved or dispersed in a small amount of water were added. This mixture was cooled to 45° C. under vigorous stirring. The acids and the salts were then dissolved in a small amount of water and were also incorporated slowly into the mixture under continuous stirring. Under further stirring the mixture was left to cool to 35-40° C. Hydrogen peroxide (in the form of an aqueous solution) was then incorporated into the formulation under stirring. Water was then added to 95 wt. %.

The comparison formulation (AV) was then topped up to 100 wt. % with water. Under further stirring the formulation was left to cool to room temperature.

The oxidizing agent preparation according to the invention (AE) was left to cool to RT under stirring, then the corresponding amount of Aerosil 200 was added and the formulation was topped up with water to 100 wt. %.

Each formulation was then introduced into a closed vessel.

2. Storage Test
Each oxidizing agent preparation (AV) (comparison) and (AE) (according to the invention) was stored in a closed vessel for 4 weeks.

| | Oxidizing agent preparation (AV) | | | |
|---|---|---|---|---|
| | (AV) | (AE1) | (AE2) | (AE3) |
| Storage, 4 weeks, −10° C. | separated | o.k. | o.k. | o.k. |
| Storage, 4 weeks, RT | o.k. | o.k. | o.k. | o.k. |

3. Viscosity
The viscosity of each oxidizing agent preparation was measured (22° C./Brookfield viscometer/spindle 4/4 rpm).

| | Oxidizing agent preparation (AV) | | | |
|---|---|---|---|---|
| | (AV) | (AE1) | (AE2) | (AE3) |
| Viscosity (22° C./Brookfield viscometer/spindle/4 rpm) [mPas] | 4950 | 5350 | 10100 | 11850 |

4. Production of Ready-to-Use Mixtures
The following coloring cream (B) was produced (all values in wt. %)

| Dye (B) | |
|---|---|
| Carbomer | 2.6 |
| Ascorbic acid | 0.2 |
| Cetearyl alcohol | 1.63 |
| Sodium cetearyl sulfate | 0.2 |
| PEG-40 Castor Oil | 0.4 |
| Disodium cocoamphodiacetate | 1.7 |
| Sodium chloride | 0.42 |
| Monoethanolamine | 7.3 |
| PEG-12 dimethicone | 0.8 |
| Sodium sulfite | 0.2 |
| p-toluenediamine, sulfate (x H2SO4) | 2.12 |
| 1,5-dihydroxynaphthalene | 0.03 |
| Resorcinol | 0.5 |
| 4-chlororesorcinol | 0.28 |
| 4-amino-2-hydroxytoluene | 0.03 |
| m-aminophenol | 0.46 |
| 3-amino-2-methylamino-6-methoxypyridine | 0.20 |
| sodium silicate 40/42 (sodium waterglass, viscous liquid) | 0.5 |
| Etidronic acid | 0.12 |
| Water (dist.) | to 100 |

Each of the oxidizing agent preparations (A) was mixed in a ratio of 1:1 with the dye (B) (100 g (A) and 100 g (B) were stirred in a mixing bowl), and in this way the ready-to-use mixture was produced. Directly after the production of this mixture, the viscosity of the corresponding ready-to-use mixture was measured (22° C./Brookfield viscometer/spindle 4/4 rpm).

| | Ready-to-use mixtures (A) + (B) | | | |
|---|---|---|---|---|
| | (AV) + (B) | (AE1) + (B) | (AE2) + (B) | (AE3) + (B) |
| Viscosity (22° C./ Brookfield viscometer/ spindle/4 rpm) [mPas] | 23500 | 26800 | 29300 | 37000 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An oxidizing agent preparation (A) for oxidatively changing the color of keratin fibers, in particular human hair, which preparation is present in the form of an oil-in-water emulsion (O/W emulsion), comprising
    (a1) an oil phase including one or more fat constituents (F),
    (a2) a water phase,
    (a3) hydrogen peroxide, and
    (a4) at least one type of fine-grain particles (P) having a mean particle size of less than 200 μm,
    wherein the oxidizing agent preparation (A) has a viscosity of from 1,000 to 18,000 mPas as measured at 22° C. using a Brookfield viscometer and a spindle 4 at 4 rpm.

2. The oxidizing agent preparation (A) according to claim 1, wherein the one or more fat constituents (F) are selected from the group consisting of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

3. The oxidizing agent preparation (A) according to claim 1, wherein the one or more fat constituents (F) are selected from the group consisting of $C_{12}$-$C_{30}$ fatty alcohols and are included in a total amount of from 0.1 to 4.5 wt. % in relation to the total weight of the oxidizing agent preparation (A).

4. The oxidizing agent preparation (A) according to claim 1, wherein the oxidizing agent preparation (A)—in relation to the total weight of the oxidizing agent preparation (A)— includes water in an amount of from 70.0 to 95.0 wt. %.

5. The oxidizing agent preparation (A) according to claim 1, wherein the hydrogen peroxide (a3) is included—in relation to the total weight of the oxidizing agent preparation (A)—at a concentration of 1.5 to 12.0 wt. %.

6. The oxidizing agent preparation (A) according to claim 1, wherein the (a4) at least one type of fine-grain particles (P) are fine-grain, powdery solids, optionally coated and/or modified, selected from the group consisting of silicon dioxide, starch, iron oxide, titanium oxide, magnesium oxide, aluminum oxide, zinc oxide, calcium aluminate, silica, magnesium silicoaluminate, magnesium metasilicate aluminate, talc, mica, zirconium oxide, colloidal kaolin, bentonite, glass, zinc laurate, microcrystalline cellulose, mother-of-pearl, carbon black, calcium carbonate, and poly-alkylsilsesquioxane.

7. The oxidizing agent preparation (A) according to claim 6, wherein the (a4) at least one type of fine-grain particles (P) are silicon dioxide and/or starch.

8. The oxidizing agent preparation (A) according to claim 1, wherein the (a4) at least one type of fine-grain particles (P) are fine-grain, powdery solids selected from the group consisting of pyrogenic silicon dioxide, silica dimethyl silylate, and aluminium starch octenylsuccinate.

9. The oxidizing agent preparation (A) according to claim 1, wherein the (a4) one or more types of fine-grain particles (P) are included in a total amount of from 0.05 to 5.0 wt. %.

10. The oxidizing agent preparation (A) according to claim 1, wherein the (a4) at least one type of fine-grain particles (P) have a mean particle size of from 10 nm to 180 μm.

11. The oxidizing agent preparation (A) according to claim 1, wherein the oxidizing agent preparation (A) is substantially free from polymers obtained by polymerization of at least one monomer selected from the group consisting of (meth)acrylic acid, (meth)acrylic acid esters, (meth)acrylamides, ethylene, propylene, styrene, vinylpyrrolidone and vinyl acetate.

12. A multi-component packaging unit or kit-of-parts for oxidatively changing the color of keratin fibers, in particular human hair, comprising, packaged separately from one another,
    a container (I) containing a cosmetic agent (A) and
    a container (II) containing a cosmetic agent (B),
    wherein
        the agent (A) in container (I) is an oxidizing agent preparation (A) according to claim 1, and
        the agent (B) is a dye including at least one oxidation dye precursor and/or at least one direct dye (D).

13. The multi-component packaging unit according to claim 12, wherein the dye (B) has a viscosity of from 10,000 to 50,000 mPas as measured at 22° C. using a Brookfield viscometer and a spindle 4 at 4 rpm.

14. The multi-component packaging unit according to claim 12, wherein the mixture of the oxidizing agent preparation (A) and the dye (B), when (A) and (B) are mixed at a ratio by weight of 1:1, has a viscosity of from 10,000 to 50,000 mPas as measured at 22° C. using a Brookfield viscometer and a spindle 4 at 4 rpm.

15. A cosmetic product for oxidatively changing the color of keratin fibers, in particular human hair, comprising:
    an oxidizing agent preparation (A), which is packaged in a container (I), wherein
    the oxidizing agent preparation (A) is an oxidizing agent according to claim 1, and
    the container (I) is embodied as a storage container and includes a multiple of the amount of oxidizing agent preparation (A) that is necessary for an individual color-changing process.

* * * * *